US009616236B2

(12) United States Patent
Mower et al.

(10) Patent No.: US 9,616,236 B2
(45) Date of Patent: Apr. 11, 2017

(54) SYSTEM AND METHOD FOR STIMULATING THE HEART VIA THE VAGUS NERVE

(71) Applicant: MR3 Medical, LLC, North Oaks, MN (US)

(72) Inventors: Morton M. Mower, Avon, CO (US); Ralph Hall, North Oak, MN (US)

(73) Assignee: MR3 MEDICAL, LLC., North Oaks, MN (US)

( * ) Notice: Subject to any disclaimer, the term of this patent is extended or adjusted under 35 U.S.C. 154(b) by 0 days.

(21) Appl. No.: 14/285,753

(22) Filed: May 23, 2014

(65) Prior Publication Data

US 2014/0350624 A1    Nov. 27, 2014

Related U.S. Application Data

(60) Provisional application No. 61/826,704, filed on May 23, 2013.

(51) Int. Cl.
*A61N 1/362* (2006.01)
*A61N 1/36* (2006.01)

(52) U.S. Cl.
CPC ........ *A61N 1/3622* (2013.01); *A61N 1/36114* (2013.01); *A61N 1/3628* (2013.01); *A61N 1/36053* (2013.01); *A61N 1/36164* (2013.01)

(58) Field of Classification Search
CPC .. A61N 1/36114; A61N 1/36585; A61N 1/37; A61N 1/36514; A61N 1/36592; A61N 1/3621; A61N 1/3622; A61N 1/365; A61N 1/36135; A61N 1/36185; A61N 1/05; A61N 1/362; A61N 1/0551; A61N 1/36053; A61N 1/3702; A61N 1/36139; A61N 1/025; A61N 1/3605; A61N 1/0476; A61N 1/3628; A61N 1/08; A61N 1/36164; A61N 1/368; A61B 5/0031; A61B 5/02; A61B 5/0402; A61B 5/02405; A61B 5/0245; A61B 5/486; A61B 5/042; A61B 5/1459; A61B 5/4836; A61B 5/686; A61B 5/0464; A61B 5/0006; A61B 5/0205; A61B 5/0468; G06F 19/3418; G06F 19/345
See application file for complete search history.

(56) References Cited

U.S. PATENT DOCUMENTS 8,005,539 B2 *   8/2011   Burnes et al. .................... 607/2
8,005,543 B2 *   8/2011   Libbus ............... A61N 1/36114
                                                          607/18

OTHER PUBLICATIONS

U.S. Appl. No. 14/740,681, filed Jun. 16, 2015, Mower.

* cited by examiner

*Primary Examiner* — Deborah Malamud
(74) *Attorney, Agent, or Firm* — Oblon, McCelland, Maier & Neustadt, L.L.P.

(57) ABSTRACT

A rules engine acquires sensor data from sensors applied to the heart to determine the presence of a rapid heartbeat. The rules engine applies rules to the sensor data to determine whether to deliver an electrical waveform to a vagus nerve. The rules engine further determines whether an electrical waveform should be applied to the heart and, if so, the type of electrical waveform.

11 Claims, 3 Drawing Sheets

SYSTEM AND METHOD FOR STIMULATING THE HEART VIA THE VAGUS NERVE

RELATED APPLICATIONS

This application claims the benefit of priority to U.S. Provisional Patent Application No. 61/826,704, entitled "System and Method for Stimulating the Heart via the Vagus Nerve" filed May 23, 2013, the entire contents of which are hereby incorporated by reference for all purposes.

BACKGROUND

The heart is divided into the right side and the left side. The right side, comprising the right atrium and ventricle, collects and pumps de-oxygenated blood to the lungs to pick up oxygen. The left side, comprising the left atrium and ventricle, collects and pumps oxygenated blood to the body. Oxygen-poor blood returning from the body enters the right atrium through the vena cava. The right atrium contracts, pushing blood through the tricuspid valve and into the right ventricle. The right ventricle contracts to pump blood through the pulmonic valve and into the pulmonary artery, which connects to the lungs. The blood picks up oxygen in the lungs and then travels back to the heart through the pulmonary veins. The pulmonary veins empty into the left atrium, which contracts to push oxygenated blood into the left ventricle. The left ventricle contracts, pushing the blood through the aortic valve and into the aorta, which connects to the rest of the body. Coronary arteries extending from the aorta provide the heart blood.

The heart's own pacemaker is located in the atrium and is responsible for initiation of the heartbeat. The heartbeat begins with activation of atrial tissue in the pacemaker region (i.e., the sinoatrial (SA) node), followed by cell-to-cell spread of excitation throughout the atrium. The only normal link of excitable tissue connecting the atria to the ventricles is the atrioventricular (AV) node located at the boundary between the atria and the ventricles. Propagation takes place at a slow velocity, but at the ventricular end the bundle of His (i.e., the electrical conduction pathway located in the ventricular septum) and the bundle braides carry the excitation to many sites in the right and left ventricle at a relatively high velocity of 1-2 m/s. The slow conduction in the AV junction results in a delay of around 0.1 seconds between atrial and ventricular excitation. This timing facilitates terminal filling of the ventricles from atrial contraction prior to ventricular contraction. After the slowing of the AV node, the bundle of His separates into two bundle branches (left and right) propagating along each side of the septum. The bundles ramify into Purkinje fibers that diverge to the inner sides of the ventricular walls. This insures the propagation of excitatory waveforms within the ventricular conduction system proceeds at a relative high speed when compared to the propagation through the AV node.

When the heart is working properly, both of its lower chambers (ventricles) pump at the same time as, and in synchronization with, the pumping of the two upper chambers (atria). Up to 40 percent of heart failure patients, however, have disturbances in the conduction of electrical impulses to the ventricles (e.g., bundle branch block or intraventricular conduction delay). As a result, the left and right ventricles are activated at different times. When this happens, the walls of the left ventricle (the chamber responsible for pumping blood throughout the body) do not contract simultaneously, reducing the heart's efficiency as a pump. The heart typically responds by beating faster and dilating. This results in a vicious cycle of further dilation, constriction of the vessels in the body, salt and water retention, and further worsening of heart failure. These conduction delays do not respond to antiarrhythmics or other drugs.

Patients who have heart failure may be candidates to receive a pacemaker. A pacemaker is an artificial device to electrically assist in pacing the heart so that the heart may pump blood more effectively. Implantable electronic devices have been developed to treat both abnormally slow heart rates (bradycardias) and excessively rapid heart rates (tachycardias). The job of the pacemaker is to maintain a safe heart rate by delivering to the pumping chambers appropriately timed electrical impulses that replace the heart's normal rhythmic pulses. The device designed to perform this life-sustaining role consists of a power source the size of a silver dollar (containing the battery), and control circuits, wires or "leads" that connect the power source to the chambers of the heart. The leads are typically placed in contact with the right atrium or the right ventricle, or both. They allow the pacemaker to sense and stimulate in various combinations, depending on where the pacing is required.

Either cathodal or anodal current may be used to stimulate the myocardium. The pulses produced by most pacemakers are typically cathodal and excitatory. That is, the cathodal pulse is of sufficient magnitude and length to cause the heart to beat. Cathodal current comprises electrical pulses of negative polarity. This type of current depolarizes the cell membrane by discharging the membrane capacitor, and directly reduces the membrane potential toward threshold level. Cathodal current, by directly reducing the resting membrane potential toward threshold has a one-half to one-third lower threshold current in late diastole than does anodal current.

Anodal current comprises electrical pulses of positive polarity. The effect of anodal current is to hyperpolarize the resting membrane. On sudden termination of the anodal pulse, the membrane potential returns towards resting level, overshoots to threshold, and a propagated response occurs. The use of anodal current to stimulate the myocardium is generally discouraged due to the higher stimulation threshold, which leads to use of a higher current, resulting in a drain on the battery of an implanted device and impaired longevity. Additionally, the use of anodal current for cardiac stimulation was discouraged due to the suspicion that the anodal contribution to depolarization can, particularly at higher voltages, contribute to arrhythmogenesis.

It has been shown that pacing in which a combination of cathodal and anodal pulses of either a stimulating or conditioning nature preserves the improved conduction and contractility of anodal pacing while eliminating the drawback of increased stimulation threshold. The result is a depolarization wave of increased speed. This increased propagation speed results in superior cardiac contraction leading to an improvement in blood flow. Improved stimulation at a lower voltage level also results in reduction in power consumption and increased life for pacemaker batteries.

Vagal nerves innervate the sinus node, the atrioventricular conducting pathways and the atrial muscle. Stimulation of either vagus nerve slows the heart by its effect on the above-mentioned structures. The latency of the response of the sinus node is very short, and the effect of a single vagal impulse depends on the phase of the cardiac cycle during which it is applied. Thus, vagal stimulation results in a peak response either in the first or the second beat after its onset.

The slowing of heart rate increases with the frequency of vagal stimulation and the relationship of this to pulse interval is linear.

Sympathetic postganglionic fibers innervate the entire heart, including the sinus node, the AV conducting pathways and the atrial and ventricular myocardium. Increased activity of the sympathetic nerves results in increase in heart rate and force of contraction. In addition, the rate of conduction through the heart is increased and the duration of contraction is shortened. When sympathetic activity increases, there is a latent period of up to five seconds before an increase in heart rate, which reaches a steady level after about 30 seconds. This is in marked contrast to vagal effects, which are almost instantaneous.

The frequency of sympathetic activity is also linearly related to heart period with the right sympathetic nerve having a greater effect on sinus node rate than the left sympathetic nerve.

SUMMARY

In an embodiment, a memory is configured to store one or more anodal waveforms, cathodal waveforms, and biphasic waveforms. A waveform or a combination of waveforms may be selected from the memory by a processor based on sensor data, data about the user and rules also stored in the memory. The stored waveforms comprise waveform data that are used by the multi-phase cardiac stimulus generator to produce waveforms for applying to the heart and/or the vagus nerve.

DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

As used herein, the term "pulse" refers to a single occurrence of an electrical signal that has a defined shaped and period.

As used herein, the term "waveform" refers to a repeating electrical signal that may include one or more pulses. The pulses that make up the waveform may be the same or may differ in any one of shape, polarity, duration and amplitude. For example, a biphasic waveform may include an anodal pulse and a cathodal pulse. The anodal and cathodal components may differ only in polarity or may be differ in shape, polarity, duration and amplitude. Pulses making up a waveform may differ in shape, polarity, duration, and amplitude but be equivalent in power.

As used herein, the term "sub-threshold waveform" refers to a waveform that does not result in stimulating the heart to beat. A waveform may be sub-threshold because the amplitude of the waveform is below an amplitude threshold value necessary to stimulate a heartbeat. A waveform may be sub-threshold because the duration of the waveform is below a duration threshold value necessary to stimulate a heartbeat. A waveform may be sub-threshold because the power of the waveform is below a power threshold value necessary to stimulate a heartbeat.

As used herein, the term "pacing waveform" refers to a waveform that stimulates a heartbeat, results in depolarization and is by definition equal to or greater than a threshold necessary to simulate a heartbeat.

Figure 1:
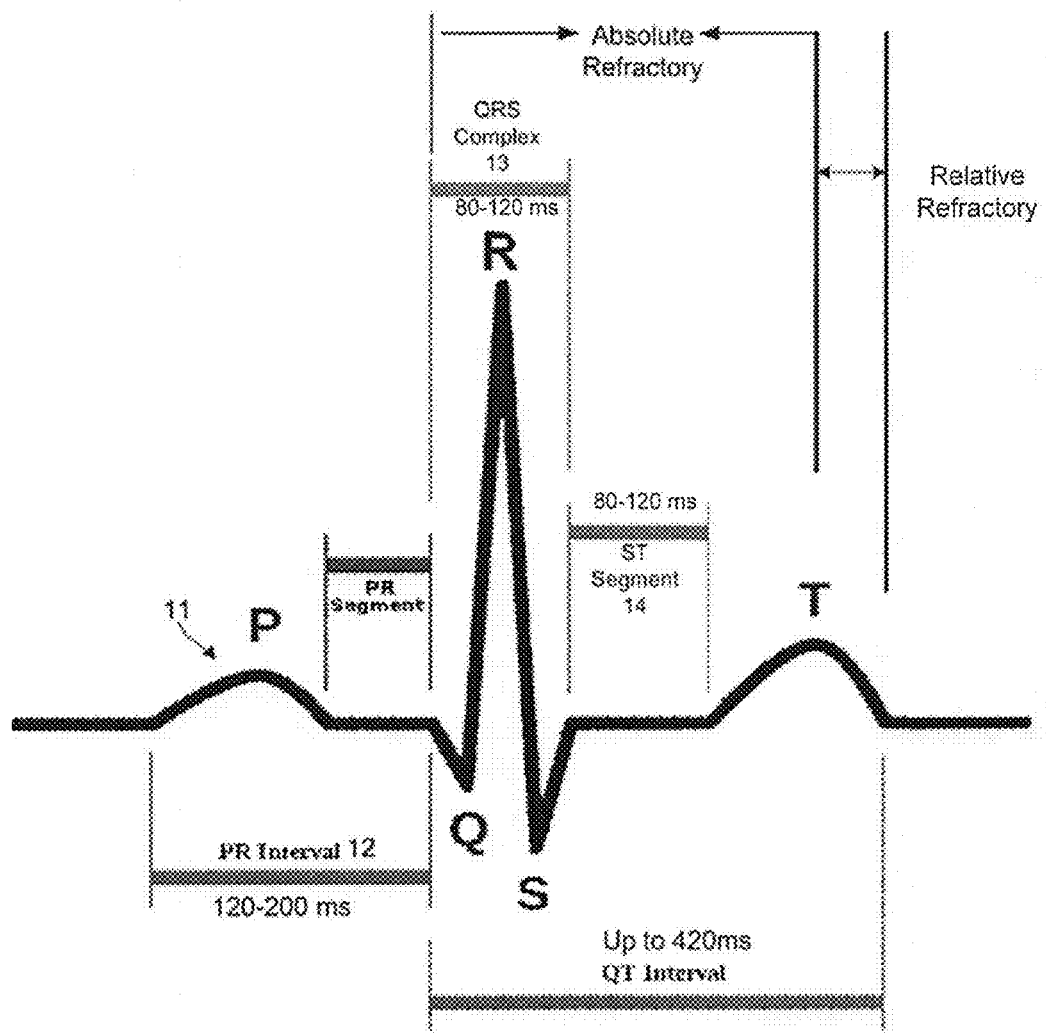
FIG. 1 is a schematic representation of the electrical activity of a typical heartbeat as is known in the prior art.

FIG. 1 shows a representative tracing 10 of electrical activity in a typical heartbeat. A P wave 11 represents the wave of depolarization that spreads from the SA node throughout the atria. A period of time from the onset of the P wave to the beginning of a QRS complex is known as the P-R interval 12. The P-R interval 12 represents the time between the onset of atrial depolarization and the onset of ventricular depolarization (typically lasting 20-200 ms). If the P-R interval is >200 ms, there is an AV conduction block, which is also known as a first-degree heart block if the impulse is still able to be conducted into the ventricles.

A QRS complex 13 represents the period of ventricular depolarization, which normally occurs very rapidly (e.g., typically lasting 80-120 ms). If the QRS complex is prolonged, conduction is impaired within the ventricles.

The isoelectric period (ST segment 14) following the QRS complex 13 is the period of time (typically lasting 80-120 ms) at which the entire ventricle is depolarized and roughly corresponds to the plateau phase of the ventricular action potential. The ST segment 14 is important in the diagnosis of ventricular ischemia or hypoxia because under those conditions, the ST segment 14 can become either depressed or elevated.

Figure 2:
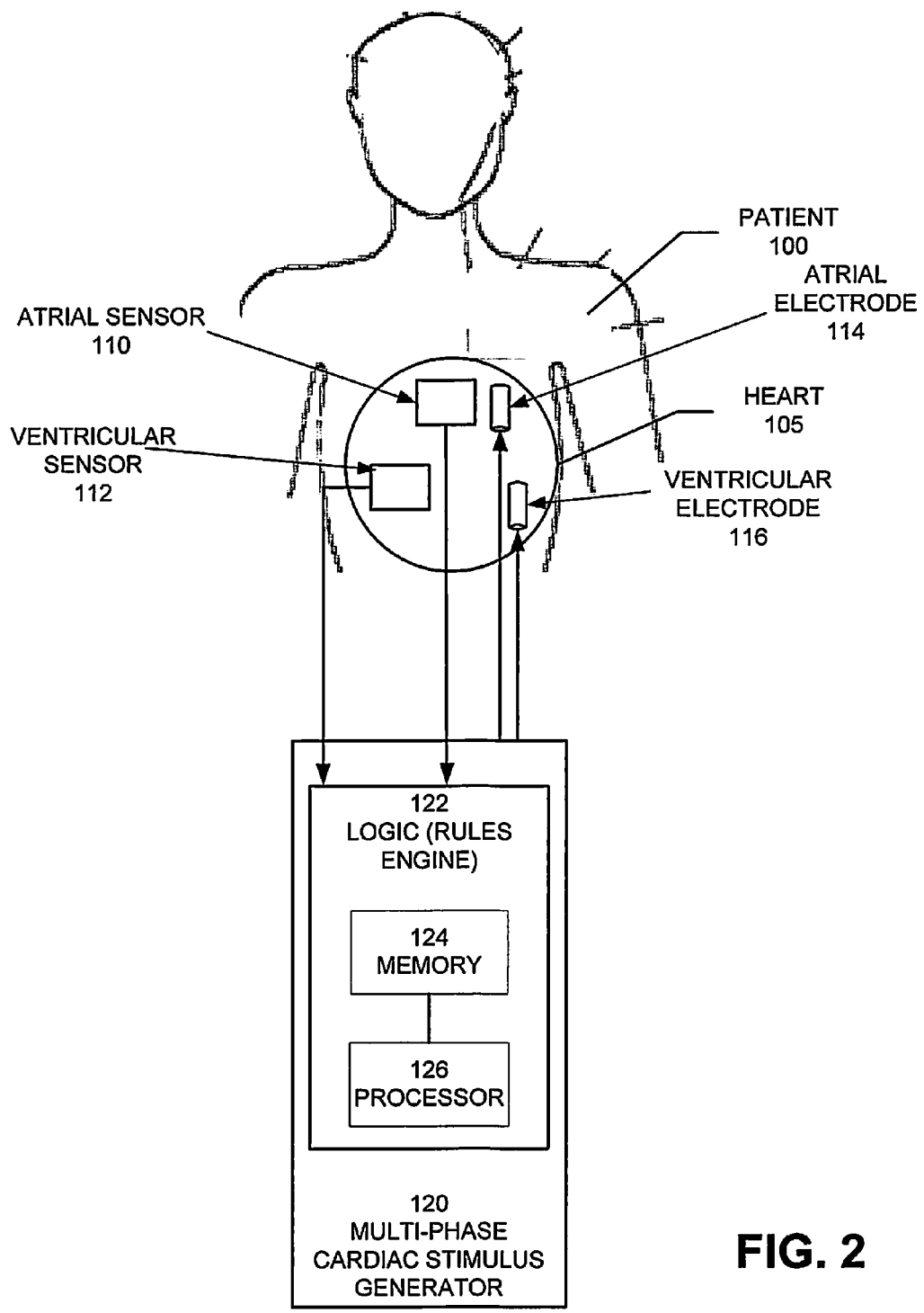
FIG. 2 is a schematic representation illustrating a cardiac stimulation device according to an embodiment.

FIG. 2 is a schematic representation illustrating a multi-phase cardiac stimulus generator 120 implanted in a patient according to an embodiment. In an embodiment, one or more sensors sense rhythm and contractions of the patient's heart 105 using at least one of atrial sensing and ventricular sensing, such as at least one of atrial sensor 110 and ventricular sensor 112. The atrial sensor 110 and/or ventricular sensor 112 provide sensor data to a rules engine 122. In an embodiment, the rules engine includes a processor 126 and a memory 124 for storing rules and receiving sensor data. The rules engine 122 may poll the one or more of the atrial sensor 110 and the ventricular sensor 112 to obtain sensor data and to apply the rules to the sensor data in order to determine whether to deliver electrical waveforms to one or more electrodes, and, if electrical waveforms are to be delivered, which of the one or more electrodes is to receive the electrical waveforms. In an embodiment, the one or more electrodes may be an atrial electrode 114 and a ventricular electrode 116, and may provide electrical waveforms to at least one of an atrial chamber and a ventricular chamber of the heart 105. The multi-phase cardiac stimulus generator 120 may generate an anodal waveform, a cathodal waveform, and a biphasic waveform above or below threshold depending on the sensor data and the rules applied by the rules engine 122.

In an embodiment, the memory 124 of the rules engine 122 of the multi-phase cardiac stimulus generator 120 is configured to store one or more anodal waveforms, cathodal waveforms, and biphasic waveforms. A waveform or a combination of waveforms may be selected from the memory 124 by the processor 126 based on sensor data and based on rules also stored in memory 124.

In an embodiment, the memory 124 may also store information about the patient 100. The processor 126 may further select a waveform or a combination of waveforms from the stored waveforms based on the sensor data and data about the user.

In an embodiment, the stored waveforms comprise waveform data that are used by the multi-phase cardiac stimulus generator 120 to produce waveforms for applying to the heart.

Figure 3:
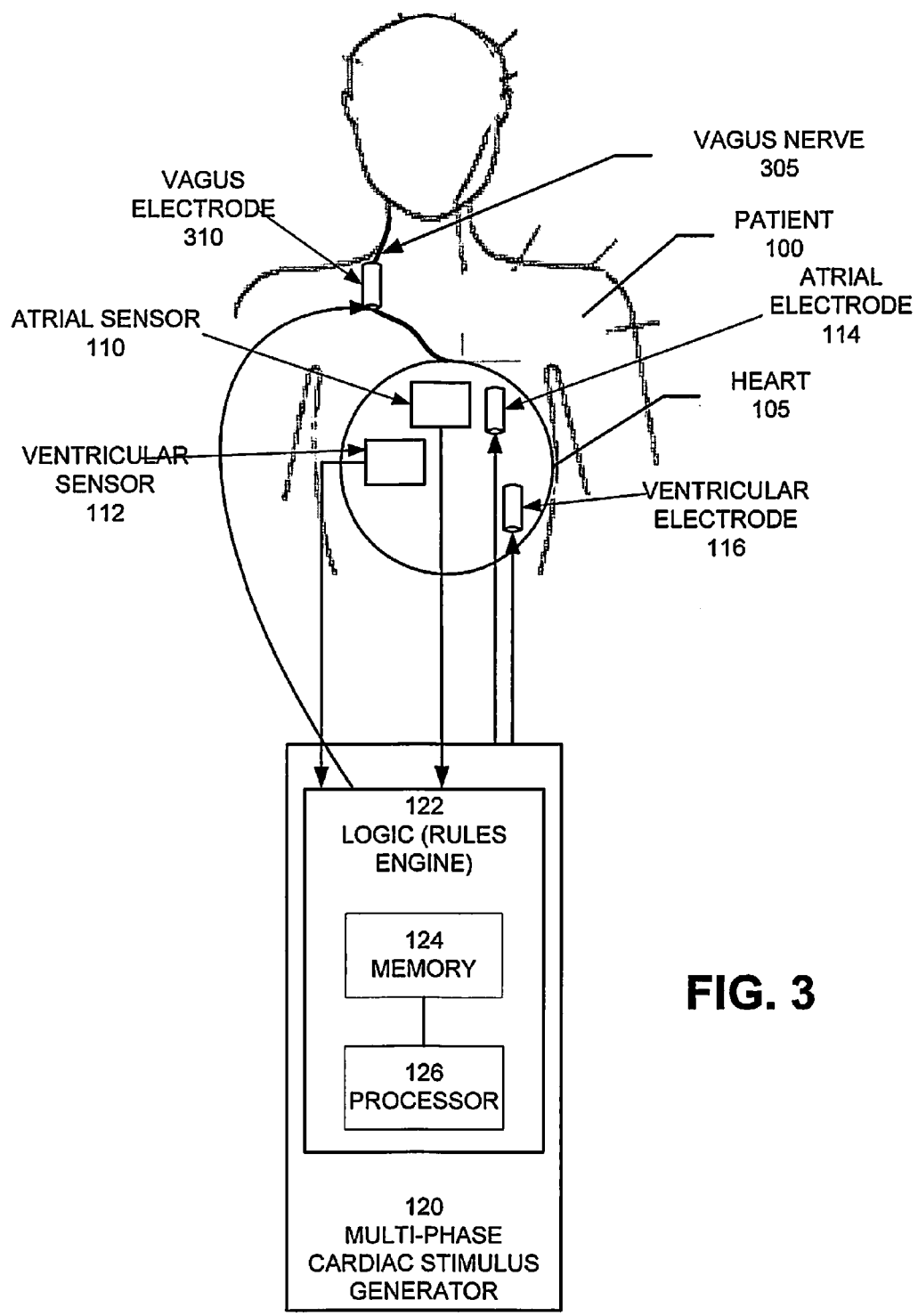
FIG. 3 is a schematic representation illustrating a cardiac and vagus nerve stimulation device according to an embodiment.

FIG. 3 is a schematic representation illustrating a cardiac and vagus nerve stimulation device according to an embodiment. FIG. 3 includes elements from FIG. 2 and additionally includes a vagus electrode 310 for stimulating the vagus nerve 305. In an embodiment, the vagus nerve 305 is accessed in the neck. The carotid sheath is dissected and the vagus electrode 310 is an encircling electrode that is wrapped around the vagus nerve 305 to receive electrical stimulation.

In an embodiment of the present invention, the one or more of atrial sensor 110 and ventricular sensor 112 provide sensor data that indicates the onset of tachycardia. In response to the heart sensor data, the rules engine 122 may apply an electrical waveform to the vagus nerve 305 via the vagus electrode 310. The rules engine 122 monitors the sensor data to determine when a sinus rhythm has been reestablished in the cardiac tissue. If a sinus rhythm has been reestablished in the cardiac tissue, the rules engine 122 halts the stimulus to the vagus electrode 310. If a sinus rhythm has not been reestablished in the cardiac tissue, the rules engine 122 continues the stimulation of the vagus nerve 305.

In an embodiment, the electrical waveform may be low frequency or high frequency electrical signal or a waveform made up of trains of electrical pulses. In an embodiment, the electrical waveform is a biphasic waveform. In another embodiment, the stimulation of the vagus nerve may be combined with the application of a sub-threshold waveform to the heart as previously described.

A system and method for reducing stroke work in an artificially paced heart have been disclosed. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. An apparatus configured to apply a therapy to a patient's heart comprising:
   a multi-phase cardiac stimulus generator;
   one or more sensors;
   one or more electrodes configured to be coupled to at least one of an atrial chamber and a ventricular chamber of the heart;
   one or more electrodes configured to encircle and contact a vagus nerve;
   a processor; and
   a memory configured to store data from the one or more sensors, waveform data, and rules that when executed by the processor cause the processor to
   detect using the one or more sensors a rapid heartbeat;
   apply the rules to the sensor data to determine whether to deliver a first electrical waveform to the vagus nerve;
   select waveform data from the memory corresponding to the first electrical waveform;
   deliver the first electrical waveform, based on the waveform selected from the memory, to the one or more electrodes configured to encircle and contact the vagus nerve;
   determine whether to deliver a sub-threshold electrical waveform to the heart via at least one of the one or more electrodes;
   instruct the multi-phase cardiac stimulus generator to generate the sub-threshold electrical waveform from the stored waveform data when it is determined to deliver the sub-threshold electrical waveform to at least one of the one or more electrodes; and
   deliver the sub-threshold electrical waveform to the one or more electrodes that are coupled to the at least one of an atrial chamber and a ventricular chamber of the heart.

2. The apparatus of claim 1, wherein the first electrical waveform is a biphasic waveform.

3. The apparatus of claim 1, wherein the sub-threshold electrical waveform is an anodal or biphasic waveform.

4. The apparatus of claim 1, wherein the memory is further configured to store patient data, and the rules further cause the processor to select the waveform data from the memory based, at least in part, on the patient data.

5. The apparatus of claim 1, wherein the rules further cause the processor to determine whether to deliver the sub-threshold electrical waveform based on whether the one or more sensors indicate that a sinus rhythm has been reestablished in the patient's heart.

6. The apparatus of claim 1, wherein rules further cause the processor to deliver a stimulating electrical waveform to the one or more electrodes configured to encircle and contact the vagus nerve while delivering the sub-threshold electrical waveform to one or more of the electrodes configured to be coupled to at least one of the atrial chamber and the ventricular chamber of the heart.

7. The apparatus of claim 1, wherein at least one of the first electrical waveform and the sub-threshold electrical waveform includes a train of pulses.

8. The apparatus of claim 1, wherein the rules further cause the processor to detect an onset of tachycardia or other undesired cardiac rhythm based on data from the one or more sensors, and to deliver the first electrical waveform to the one or more electrodes configured to encircle and contact the vagus nerve when the onset of tachycardia is detected.

9. The apparatus of claim 1, wherein the sub-threshold electrical waveform is delivered while the first electrical waveform is delivered.

10. The apparatus of claim 1, wherein the sub-threshold electrical waveform is a waveform that is insufficient to cause the patient's heart to beat.

11. The apparatus of claim 1, wherein the sub-threshold electrical waveform is delivered after delivery of the first waveform is completed.

* * * * *